(12) United States Patent
Mecea

(10) Patent No.: US 9,267,924 B2
(45) Date of Patent: Feb. 23, 2016

(54) METHOD FOR DETECTING GAS AND A GAS DETECTOR THEREFOR

(75) Inventor: Vasile Mecea, Järfälla (SE)

(73) Assignee: QCM LAB AKTIEBOLAG, Jarfalla (SE)

( * ) Notice: Subject to any disclaimer, the term of this patent is extended or adjusted under 35 U.S.C. 154(b) by 525 days.

(21) Appl. No.: 13/640,755

(22) PCT Filed: Apr. 15, 2010

(86) PCT No.: PCT/SE2010/000097
§ 371 (c)(1),
(2), (4) Date: Oct. 12, 2012

(87) PCT Pub. No.: WO2011/129723
PCT Pub. Date: Oct. 20, 2011

(65) Prior Publication Data
US 2013/0031956 A1 Feb. 7, 2013

(51) Int. Cl.
*G01N 29/02* (2006.01)
*G01N 21/00* (2006.01)
*G01N 22/00* (2006.01)
*G01N 23/00* (2006.01)
*G01N 7/00* (2006.01)
*G01N 29/024* (2006.01)
*G01N 29/34* (2006.01)
*G01N 29/036* (2006.01)

(52) U.S. Cl.
CPC ............ *G01N 29/024* (2013.01); *G01N 29/036* (2013.01); *G01N 29/348* (2013.01); *G01N 2291/021* (2013.01); *G01N 2291/02809* (2013.01); *G01N 2291/045* (2013.01); *G01N 2291/101* (2013.01)

(58) Field of Classification Search
None
See application file for complete search history.

(56) References Cited

U.S. PATENT DOCUMENTS

| 2,536,025 | A | | 1/1951 | Blackburn |
| 3,482,647 | A | | 12/1969 | Lynch et al. |
| 3,697,936 | A | | 10/1972 | Zacharias, Jr. et al. |
| 5,411,709 | A | * | 5/1995 | Furuki et al. ............ 422/91 |

(Continued)

FOREIGN PATENT DOCUMENTS

| WO | WO 02/29400 A2 | 4/2002 |
| WO | WO 2008/114003 A1 | 9/2008 |

OTHER PUBLICATIONS

International Search Report Corresponding to International Application No. PCT/SE2010/000097; Date of Mailing: Dec. 20, 2010; 4 Pages.

(Continued)

*Primary Examiner* — Peter Macchiarolo
*Assistant Examiner* — Jermaine Jenkins
(74) *Attorney, Agent, or Firm* — Myers Bigel & Sibley, P.A.

(57) ABSTRACT

It is presented a method for detecting a gas (G). Acoustic waves ($W_t$) are generated and transmitted via a wave generating and sensing means (2) towards a reflecting wall (3) and thereafter reflected acoustic waves ($W_r$) are detected by the wave generating and sensing means (2) wherein a presence of the gas (G) is detected by determining a change in an output signal of the wave generating and sensing means (2). A gas detector (1) is also presented.

15 Claims, 4 Drawing Sheets

(56) References Cited

U.S. PATENT DOCUMENTS

| | | |
|---|---|---|
| 5,557,047 A | 9/1996 | Koide |
| 5,753,797 A * | 5/1998 | Forster et al. ............ 73/24.01 |
| 5,869,749 A * | 2/1999 | Bonne et al. ............ 73/53.01 |
| 5,886,249 A * | 3/1999 | Bonne et al. ............ 73/24.02 |
| 6,094,987 A * | 8/2000 | Suzuki et al. ............ 73/597 |
| 6,227,040 B1 * | 5/2001 | Hastings et al. ............ 73/54.41 |
| 6,250,137 B1 | 6/2001 | Takahashi et al. |
| 6,260,408 B1 | 7/2001 | Vig et al. |
| 6,770,032 B2 * | 8/2004 | Kaplan ............ 600/437 |
| 7,965,017 B2 * | 6/2011 | Iwashita et al. ............ 310/321 |
| 2005/0109080 A1 | 5/2005 | Hok |
| 2008/0011060 A1 | 1/2008 | Lynnworth |
| 2012/0184051 A1 * | 7/2012 | Nirschl ............ 436/501 |

OTHER PUBLICATIONS

Extended European Search Report Corresponding to European Application No. 10849931.0; Date of Mailing: Sep. 5, 2013; 9 Pages.

Granstedt at al., "Gas sensor with electroacoustically coupled resonator," Sensors Actuators B 78:161-165 (2001).

Mecea, "Tunable gas sensors," Sensors Actuators B 15-16:265-269 (1993).

\* cited by examiner

METHOD FOR DETECTING GAS AND A GAS DETECTOR THEREFOR

RELATED APPLICATIONS

This application is a 35 U.S.C. §371 national phase application of PCT Application PCT/SE2010/000097, filed Apr. 15, 2010. The entire content of this application is incorporated herein by reference.

TECHNICAL FIELD

The invention generally relates to the field of gas detection. In particular, the invention relates to a method for detecting gas by means of acoustic waves propagating in a gas to be detected, and to a gas detector.

BACKGROUND

Gas is a valuable natural resource and it is of interest to detect leakage of gas both from an economic aspect as well as for the hazard a leaking gas may present to its surroundings.

Current gas detection methods may for instance depend on absorption of e.g. wavelengths of electromagnetic radiation, with different gases having different absorption spectra, on chemical reactions, changes in electrical conductivity or in the capacitance of thin film.

A drawback with these methods is that the kinetic of gas absorption is quite slow, thereby limiting the field of application of these absorption methods.

Faster methods are based on the physical properties of various gases. Thermal conductivity is used for gas sensing in chromatography and optical absorption in the infrared region of the spectrum is used for carbon dioxide detection. For hydrogen detection there are methods that use catalysts. However, in contact with other gases the catalyst can be poisoned and the response of the detector is dramatically reduced.

Some known methods utilize the phenomenon of resonance in a resonance cavity to detect the presence of a gas in the resonance cavity. Resonance occurs when a distance d between a reflecting wall and e.g. an oscillator that transmits waves in the cavity, is an integer of half wavelengths, i.e.

$$d = n\frac{\lambda}{2} \quad (1)$$

where n=1, 2, 3 .... The wavelength of a vibration in a gas is dependent of the gas because the sound velocity is different in different gases, the wavelength being given by the relation:

$$\lambda = \frac{v}{f} \quad (2)$$

where v is the sound velocity and f is the vibration frequency.

An ultrasonic method utilizing resonance has been described in the article "A gas analysis instrument based on sound velocity measurements" by E. Griffiths published in the Proceedings of the Physical Society, 1926. The article describes a quartz crystal and a reflecting wall parallel to the quartz crystal, which together form a resonance cavity. The quartz crystal can generate mechanical longitudinal waves in the cavity, with a 40 kHz frequency. Resonance in the cavity is detected by an increase in the anode current of an oscillating circuit which comprises the quartz crystal. By measuring the distance between adjacent resonances, i.e. a half wavelength, sound velocity in different gases is determined as well as the concentration of a gas in a gas mixture.

However, none of the above presented methods can be used for measurements of low gas concentration.

SUMMARY

In view of the above, an object is to provide a gas detection method and a gas detector for detecting low concentrations of gas.

The general idea of the invention is to utilize that the propagation speed and hence the wavelength of an acoustic wave propagating in a gas depends on the properties of the gas, i.e. for different gases a wave with a frequency f will have different speed of propagation and hence different wavelengths.

Hence, according to a first aspect of the present invention there is provided a method for detecting a gas in a gas detector, the gas detector having a reflecting wall and a wave generating and sensing means at a distance d opposite the reflecting wall, wherein the method comprises a continuous process of:

generating acoustic waves by means of the wave generating and sensing means, transmitting the acoustic waves through the gas towards the reflecting wall, wherein the acoustic waves are reflected towards the wave generating and sensing means from the reflecting wall, thereby creating and destructive interference between the acoustic waves propagating in opposite directions, the constructive and destructive interference being dependent of a wavelength of the acoustic waves, which wavelength is dependent of the gas, detecting the acoustic waves by the wave generating and sensing means, wherein a motional resistance of the wave generating and sensing means is changed due to a change of the wavelength of the acoustic waves, and indicating a presence of the gas by determining a change of a magnitude of an output signal of the wave generating and sensing means, wherein the change of the magnitude of the output signal is related to the change of the motional resistance.

The output signal may vary in response to detecting the waves because a motional resistance of the wave generating and sensing means typically is dependent of resonance and hence the wavelength of the waves propagating between the wave generating and sensing means and the reflecting wall. Hence, as the motional resistance changes, the output of the wave generating and sensing means changes.

Hereto, by means of the invention it may be possible to detect low concentrations of the gas in e.g. an environment mainly comprising a gas of a second type, a reference gas.

The generating may comprise generating acoustic waves with a constant frequency in the range 0.5 MHz to 500 MHz, preferably in the range 0.5 MHz to 50 MHz. By transmitting waves with such a short wavelength, the sensitivity of gas detection increases because any changes of the (short) wavelength indicate the presence of a gas.

One embodiment may further comprise setting the distance d at a fixed position such that the magnitude of the output signal is less than a magnitude of the output signal when resonance occurs between the reflecting wall and the wave generating and sensing means. When the distance d is set so that the magnitude of the output signal is near a resonance peak, i.e. on the slope of a resonance peak, the output signal of the wave generating and sensing means becomes very sensitive to any changes in the detected wavelength. Hence, by setting the distance d so that the magnitude of the output signal is on the slope of the resonance peak, even small concentrations of gas between the sensor and the reflecting wall will provide an increase in the output signal due to the gas dependent change in the wavelength of the transmitted waves. Thus, the gas detector becomes very sensitive and is able to detect low concentrations of gas.

The resonance may occur for acoustic waves propagating in a reference gas. For example, a distance between the reflecting wall and the wave generating and sensing means may be determined for resonance of the waves in a reference gas such as air, wherein the distance d is set so that the output signal from the wave generating and sensing means is slightly less, preferably about half of the magnitude of the resonance peak when the resonance for air occurs. In a gas such as helium waves have a longer wavelength compared to when propagating in air, thus the wavelengths are longer in helium than in air, and hence the output signal increases when helium is present, thereby indicating the presence of helium.

One embodiment may comprise compensating for temperature changes in the gas detector. The wavelength of a mechanical longitudinal wave is temperature dependent, and therefore compensation of temperature changes may provide a more accurate gas detector. Hence, in one embodiment the compensating may comprise moving a reflecting surface of the reflecting wall along an axis transverse to the reflecting surface, thereby adjusting the distance d between the reflecting wall and the wave generating and sensing means.

Beneficially, the moving may comprise wherein the moving comprises automatically moving the reflecting wall by means of thermal expansion properties of materials used for constructing the gas detector.

According to a second aspect of the present invention there is provided a gas detector arranged to detect gas, the gas detector comprising: a wave generating and sensing means; and a reflecting wall opposite the wave generating and sensing means, wherein the wave generating and sensing means is arranged to generate acoustic waves to propagate between the wave generating and sensing means and the reflecting wall, and to detect acoustic waves reflected by the reflecting wall, wherein the reflecting wall and the wave generating and sensing means are fixedly arranged in the gas detector.

The distance d may be in the range of approximately $\lambda/2$ to approximately $50*\lambda$, where $\lambda$ denotes the wavelength of the acoustic waves. The term approximately is herein defined as the distance d may be slightly less or more than an integer multiple of the wavelength as already elaborated above in terms of resonance with regards to setting the distance d such that the magnitude of the output signal is slightly less than the magnitude of the output signal when resonance occurs between the reflecting wall and the opposite wall defined by a resonator surface of the wave generating and sensing means.

Further features and advantages of the present invention will be evident from the following description.

BRIEF DESCRIPTION OF THE DRAWINGS

The invention and further advantages thereof will now be described by a non-limiting example of an embodiment with reference to the accompanying drawings.

DETAILED DESCRIPTION

Figure 1:
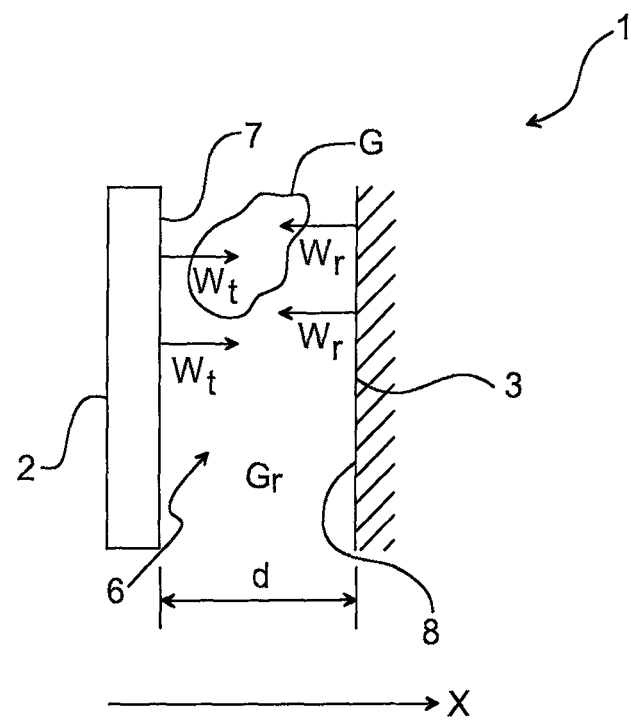
FIG. 1 shows a schematic view of a cavity of an embodiment of a gas detector according to the invention.

In the following description, for purpose of explanation and not limitation, specific details are set forth, such as particular techniques and applications in order to provide a thorough understanding of the present invention. However, it will be apparent for a person skilled in the art that the present invention may be practiced in other embodiments that depart from these specific details. In other instances, detailed description of well-known methods and apparatuses are omitted so as not to obscure the description of the present invention with unnecessary details.

With reference to FIGS. 1-6, an example of a gas detector 1 according to the invention will now be described in more detail. The gas detector 1 comprises a wave generating and sensing means 2, and a reflecting wall 3 positioned at a distance d opposite and in parallel with the wave generating and sensing means 2. The wave generating and sensing means 2 is an assembly comprising a piezoelectric resonator and an electronic oscillator for the continuous generation of acoustic waves. The wave generating and sensing means 2 may be electrically coupled to a power source (not shown), such as a battery, so as to provide power to the gas detector 1 during operation thereof.

In the present exemplifying embodiment, the wave generating and sensing means 2 comprises a piezoelectric resonator coupled to an electronic oscillator. The piezoelectric resonator may comprise e.g. a quartz crystal, or other piezoelectric resonator that can generate acoustic waves in a surrounding gas.

A resonator surface 7 of the piezoelectric resonator forms a resonant cavity 6 with the reflecting wall 3. By attaching an electronic oscillator to the piezoelectric resonator, the resonator surface 7 starts to oscillate and thereby generate and transmits acoustic waves towards the reflecting wall 3.

Waves $W_t$ generated and transmitted by the wave generating and sensing means 2 may propagate in the resonant cavity 6 through a gas G, which gas G is schematically illustrated as a cloud in FIG. 1 although it normally mixes with a reference gas $G_r$. The reference gas $G_r$ is to be construed as a gas which is a dominating gas surrounding the gas detector 1 and is usually not the gas that is to be detected. The reference gas $G_r$ may typically be air.

The acoustic waves typically propagate in directions parallel to an X-axis transverse to a reflecting surface 8 of the reflecting wall 3. The acoustic waves $W_r$ are reflected towards the wave generating and sensing means 2 by the reflecting wall 3 for detection thereof by the wave generating and sensing means 2. The detected waves $W_r$ increase the motional resistance of the wave generating and sensing means 2, as vibration energy is absorbed by the wave generating and sensing means 2, thereby increasing the output voltage, i.e. the output signal of the oscillator because the current from the oscillator is constant. The presence of the gas G in a reference gas $G_r$ is hence detected as a consequence of determining the change in the output signal.

Figure 2:
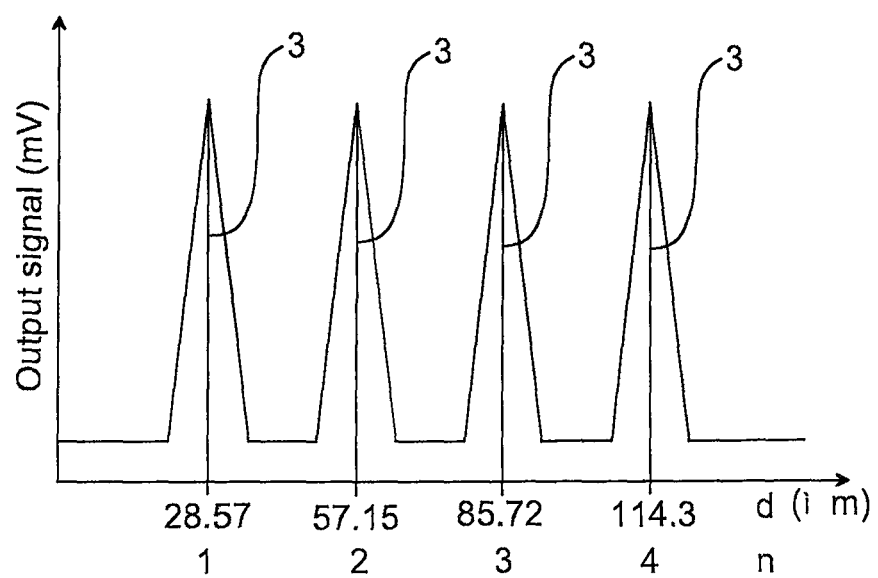
FIG. 2 illustrates an example of resonance when air is the gas present in the gas detector of FIG. 1.

FIG. 2 illustrates an example of a response of the output signal of the wave generating and sensing means 2. The reflecting wall 3 has in the graph of FIG. 2 been moved continuously along the X-axis thereby illustrating the output signal for different distances d between the resonator surface 7 of the wave generating and sensing means 2 and the reflecting wall 3 with the acoustic waves propagating in air. The numerical values are calculated in the resonant cavity 6 for waves with a 6 MHz frequency at 20° C., with n being the interference order.

Figure 3:
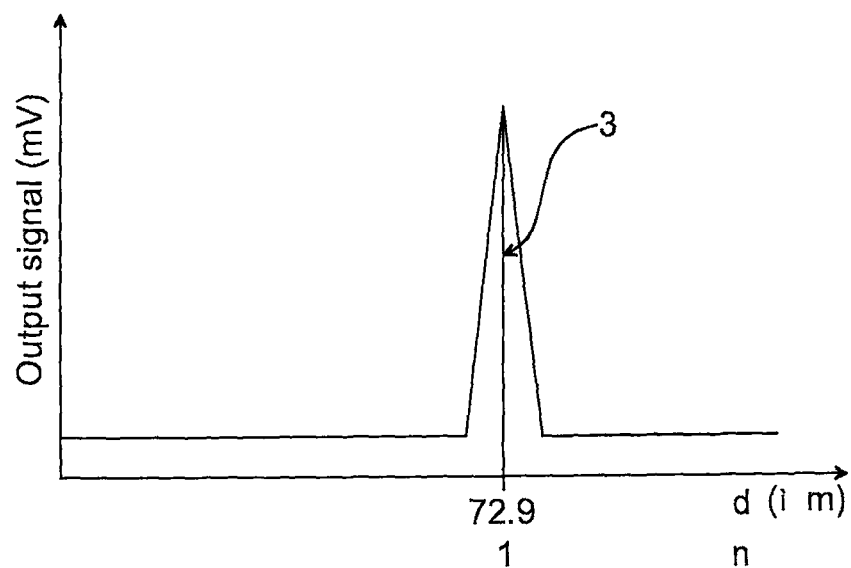
FIG. 3 illustrates another example of resonance when helium is present in the gas detector of FIG. 1.

FIG. 3 illustrates an example of a response of the output signal of the wave generating and sensing means 2. The reflecting wall 3 has in the graph of FIG. 3 been moved continuously along the X-axis thereby illustrating the output signal for different distances d between the resonator surface 7 of the wave generating and sensing means 2 and the reflecting wall 3 with the acoustic waves propagating in helium. The numerical values are calculated in the resonant cavity 6 for waves with a 6 MHz frequency in a helium environment at 20° C. for n=1.

Figure 4:
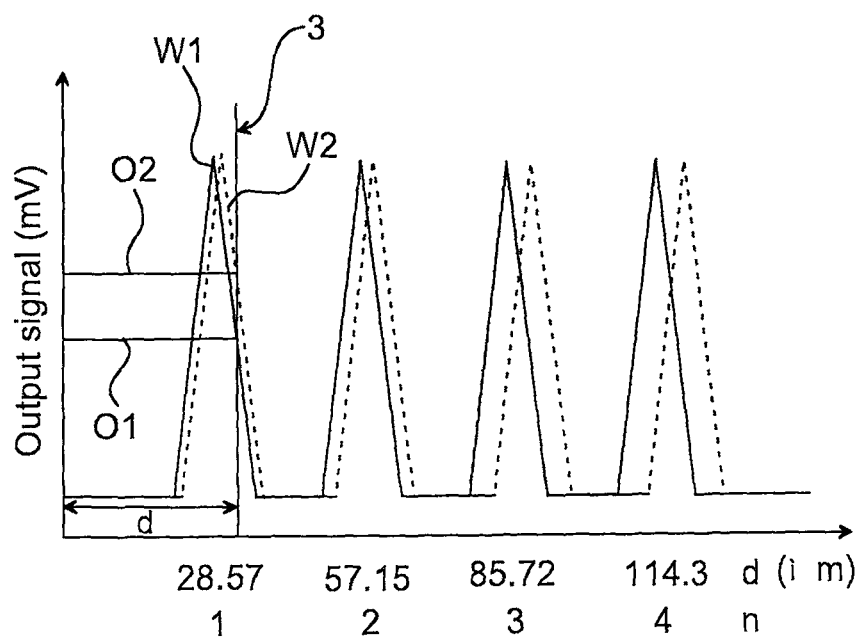
FIG. 4 illustrates shifts of the resonance peaks in the cavity of FIG. 1 when a mixture of two types of gases is present in the cavity.

FIG. 4 illustrates shifts of the resonance peaks, i.e. the magnitude of the output signal of the wave generating and sensing means 2 at resonance in the resonant cavity 6. In the present example a small concentration of helium is present in the reference gas $G_r$ exemplified by air and contained in the resonant cavity 6. Hence helium exemplifies the gas G.

The solid lined curve W1 shows the resonance peaks for acoustic waves propagating in air and the broken lined curve W2 shows slightly shifted resonance peaks with acoustic waves propagating through the air containing a small quantity of gas G (helium). It can be seen from Table 1 below that the wave propagation speed is higher in helium than in air. Therefore, the wavelength is longer as shown in Table 1 and apparent from equation (2) above. Hence the curve W2 is shifted towards longer wavelengths. For each number n of the resonance peaks, the translation of the curve W2 becomes greater compared to the curve W1. As can be seen, an output signal O1 of the wave generating and sensing means increases to O2 for the curve W2. Further, the sensitivity of gas detection increases with each resonance peak n as the shift, and hence the difference between the output signals O1 and O2, becomes greater with each resonance peak.

The following table gives examples of the acoustic wave speed of propagation, wavelength and half wavelength, at 6 MHz and 20° C. in some gases.

TABLE 1

| Gas | Sound velocity (m/s) | Wavelength (μm) | Halfwavelength (μm) |
| --- | --- | --- | --- |
| Air | 342.9 | 57.15 | 28.57 |
| $CO_2$ | 268.3 | 44.72 | 22.36 |
| $O_2$ | 327.4 | 54.57 | 27.28 |
| $N_2$ | 345.6 | 57.60 | 28.80 |
| He | 999.7 | 166.62 | 83.31 |
| $H_2$ | 1336.4 | 222.73 | 111.36 |

In order to compensate for the temperature dependence of a wavelength of an wave when propagating in gas, the gas detector 1 may be constructed from materials with different thermal expansion properties, with the dimensions of the material being selected so as to provide a thermo compensation effect of the distance d when subject to temperature changes. The temperature dependence of the propagation speed of the wave in a gas is given by $$v = v_0\sqrt{(1+a\Delta t)}$$

where a=(1/273.15)° C.$^{-1}$=0.00366° C.$^{-1}$, $v_0$ is the propagation speed at 0° C., and $\Delta t$ is the difference in temperature, i.e. current temperature subtracted by 0. For a constant frequency of transmitted waves $W_t$ this effect is transferred to the half wavelength:

$$\frac{\lambda}{2} = \left(\frac{\lambda}{2}\right)_n \sqrt{(1+\alpha\Delta t)}$$

By utilizing the thermo compensating effect, the reflecting surface 8 of the reflecting wall 3 may automatically move in a direction parallel to the X-axis shown in FIG. 1 to follow the increase of the wavelength with temperature. Thereby the distance d may be adjusted automatically in order to achieve an optimal cavity length to enable measurements of very low gas concentrations for different temperatures. This may be possible by choosing appropriate materials and geometrical dimensions to exploit the thermal expansion properties of different materials. Such materials may for instance be steel, aluminium, copper, brass, glass, ceramics or amorphous quartz.

Prior to use of the gas detector 1, the distance d between the reflecting wall 3 and the wave generating and sensing means 2 can be set by connecting the reflecting wall 3 to a micrometer (not shown). By rotating the micrometer it is possible to adjust the distance d. A position of the reflecting wall 3 in relation to the wave generating and sensing means 2 is chosen, corresponding to about half of the magnitude of the resonance peak, i.e. magnitude of the output signal of the wave generating and sensing means 2 at resonance.

Alternatively, the distance d may be set by means of a piezoelectric actuator by continuously scanning a voltage applied to the actuator to thereby change the position of the reflecting wall 3.

The distance d is preferably set to be in the range of approximately λ/2 to approximately 50*λ. In other words the distance d is preferably set to be approximately in the range from the first resonance peak to the $100^{th}$ resonance peak.

The magnitude of the output signal is defined as the difference between the maximum value of the voltage, corresponding to the top of the resonance peak, and the voltage corresponding to the bottom of the resonance peak. The magnitude of the resonance peak can depend on the nature of the gas G, but is also depending on the number of the resonance n=1, 2, 3 . . . . For example the resonance peak has the greatest magnitude for n=1 and is much smaller for n=20.

The number of the resonance is preferably selected to correspond to the best temperature compensation. This is largely dependent on the thermal expansion coefficients of the materials used for the construction of the gas detector 1.

An example of how to set the distance d is given below. First the reflecting wall 3 is put in contact with the wave generating and sensing means 2 and an output voltage, higher than the resonance peak, is recorded. Then the micrometer is rotated so that the reflecting wall 3 is moved away from the wave generating and sensing means 2 along the X-axis. During this movement the resonance peaks are revealed. The micrometer is stopped at about half the height or magnitude of a certain peak, typically on its descending slope.

Figure 5:
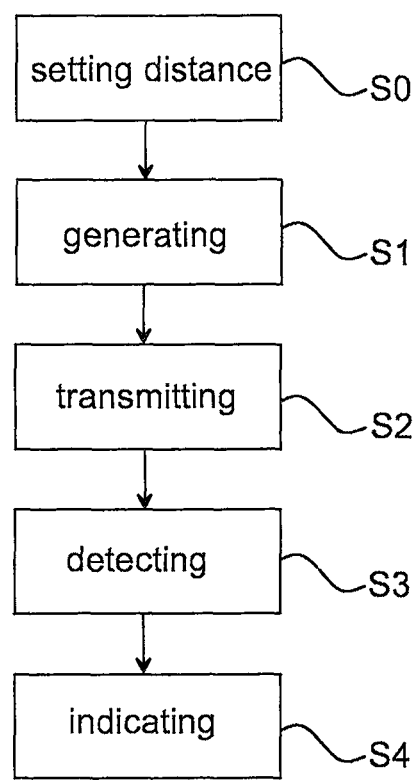
FIG. 5 illustrates a flow chart of a method to detect gas in the gas detector of FIG. 1.

With reference to FIG. 5 a flow chart of a method to detect gas in the gas detector 1 is shown.

In a step S0 the distance d is set at a fixed position such that the magnitude of the output signal is less than a magnitude of the output signal when resonance occurs between the reflecting wall and the wave generating and sensing means.

In a step S1 acoustic waves are generated by means of the wave generating and sensing means 2, In a step S2 the acoustic waves $W_t$ are transmitted through the gas as the propagation of pressure changes in the gases G and $G_r$, resulting from the oscillating resonator surface 7, towards the reflecting wall 3, wherein the acoustic waves $W_r$ are reflected towards the wave generating and sensing means 2 from the reflecting wall 3, thereby creating stationary waves through constructive and destructive interference between the acoustic waves $W_t$, $W_r$ propagating in opposite directions.

In a step S3 the acoustic waves $W_r$ are detected by the wave generating and sensing means 2, wherein a motional resistance of the wave generating and sensing means 2 is changed due to a change of the wavelength of the acoustic waves $W_t$, $W_r$.

In a step S4 a presence of the gas G is indicated by determining a change of the magnitude of the output signal of the wave generating and sensing means 2.

The wave generating and sensing means 2 and the reflecting wall 3 are preferably fixedly arranged, at least during the determining of any changes in the output signal of the wave generating means 4. As an example, a voltage meter may be utilized for determining the change in the magnitude of the output signal.

In an additional step S5, which may be carried out at any time necessary, any temperature changes are compensated for. The step S5 of compensating may comprise moving the reflecting surface 8 of the reflecting wall 3 along the axis X being transverse to the reflecting surface 8, thereby adjusting the distance d between the reflecting wall 3 and the wave generating means 2. The moving may comprise automatically moving the reflecting wall 3 by means of thermal expansion properties of materials used for constructing the gas detector 1.

Figure 6:
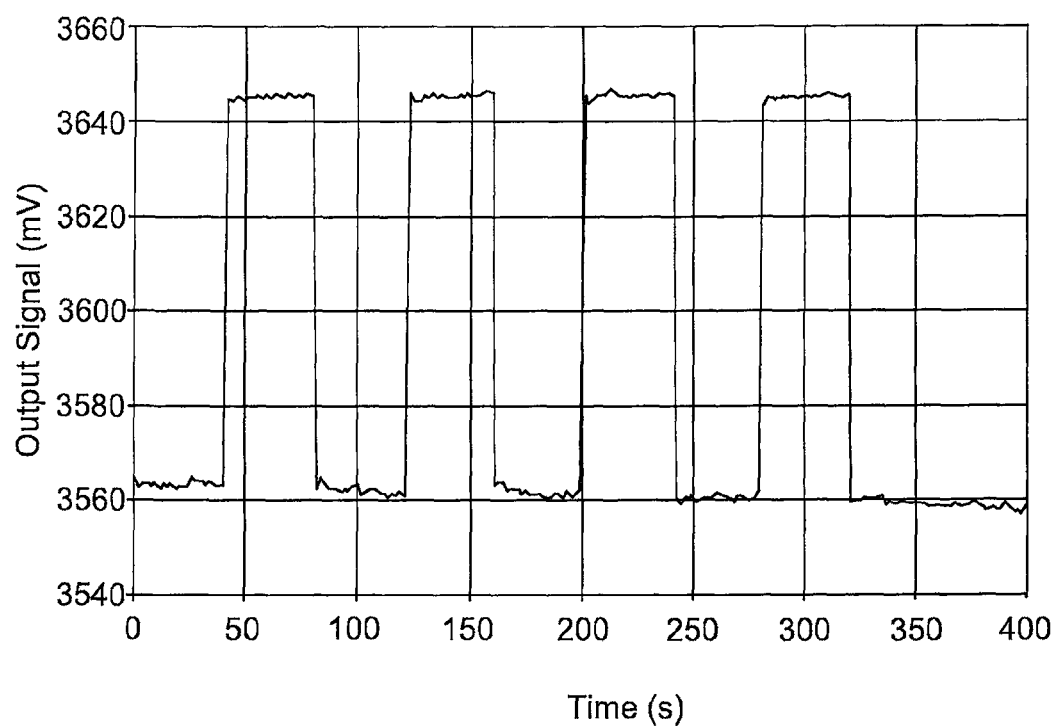
FIG. 6 shows some experimental results utilizing the gas detector in FIG. 1.

FIG. 6 shows measurement results when detecting helium in an air environment with the above-described embodiment of the gas detector 1. The increase in the output signal of the wave generating and sensing means 2 corresponds to a sudden increase of the helium concentration in air to 1200 ppm in volume. Typically, the detection limit of the gas detector 1 is about 40 ppm of volume helium in air.

Applications of the method and gas detector 1 presented herein may include, but are not limited to, gas detection in an inside environment, in an outside environment, to stationary gas detectors and portable gas detectors.

It will be obvious that the present invention may be varied in a plurality of ways. Such variations are not to be regarded as departure from the scope of the present invention as defined by the appended claims. All such variations as would be obvious for a person skilled in the art are intended to be included within the scope of the present invention as defined by the appended claims.

The invention claimed is:

1. A method for detecting a gas (G) in a gas detector (1), the gas detector (1) having a reflecting wall (3) and a wave generating and sensing means (2) at a distance d opposite the reflecting wall (3), wherein the method comprises a continuous process of:
   generating (S1) acoustic waves by means of the wave generating and sensing means (2),
   transmitting (S2) the acoustic waves ($W_t$) through the gas (G) towards the reflecting wall (3), wherein the acoustic waves ($W_r$) are reflected towards the wave generating and sensing means (2) from the reflecting wall (3), thereby creating constructive and destructive interference between the acoustic waves ($W_t$, $W_r$) propagating in opposite directions, the constructive and destructive interference being dependent of a wavelength of the acoustic waves ($W_t$, $W_r$), which wavelength is dependent of the gas (G),
   detecting (S3) the acoustic waves ($W_r$) by the wave generating and sensing means (2), wherein a motional resistance of the wave generating and sensing means (2) is changed due to a change of the wavelength of the acoustic waves ($W_t$, $W_r$), and
   indicating (S4) a presence of the gas (G) by determining a change of a magnitude of an output signal of the wave generating and sensing means (2), wherein the change of the magnitude of the output signal is related to the change of the motional resistance;
   the method further comprising compensating (S6) for temperature changes in the gas detector (1);
   wherein the compensating (S6) comprises moving a reflecting surface (8) of the reflecting wall (3) along an axis (X) transverse to the reflecting surface (8), thereby adjusting the distance d between the reflecting wall (3) and the wave generating and sensing means (2).

2. The method as claimed in claim 1, wherein the generating (S0) comprises generating acoustic waves with a constant frequency.

3. The method as claimed in claim 2, wherein the constant frequency is in the range 0.5 MHz to 500 MHz.

4. The method as claimed in claim 1, further comprising setting (S0) the distance d at a fixed position such that the magnitude of the output signal is less than a magnitude of the output signal when resonance occurs between the reflecting wall (3) and the wave generating and sensing means (2).

5. The method as claimed in claim 4, wherein the resonance occurs for acoustic waves propagating in a reference gas ($G_r$).

6. The method as claimed in claim 4, wherein setting the distance d comprises adjusting a position of the reflecting wall along an axis (X) by means of a micrometer or a piezoelectric actuator.

7. The method as claimed in claim 1, wherein the moving comprises automatically moving the reflecting wall (3) by means of thermal expansion properties of materials used for constructing the gas detector (1).

8. A gas detector (1) arranged to detect gas (G) in a reference gas ($G_r$), the gas detector (1) comprising:
   a wave generating and sensing means (2) comprising a piezoelectric resonator having a resonator surface (7), and an electronic oscillator, the piezoelectric resonator being coupled to the electronic oscillator which is arranged to feed a constant current to the piezoelectric resonator, and
   a reflecting wall (3) opposite the wave generating and sensing means (2) the resonator surface (7) forming a resonant cavity (6) with the reflecting wall (3), wherein the wave generating and sensing means (2) is arranged to generate acoustic waves to propagate between the wave generating and sensing means (2) and the reflecting wall (3), and to detect acoustic waves reflected by the reflecting wall (3), wherein the detected waves increase a motional resistance of the wave generating and sensing means (2) if the gas (G) is present in the reference gas ($G_r$), as vibration energy is absorbed by the wave generating and sensing means (2), thereby increasing the output voltage of the electronic oscillator, wherein a presence of a gas (G) in the reference gas ($G_r$) is detected as a consequence of determining a change in the output voltage, and wherein the reflecting wall (3) and the wave generating and sensing means (2) are fixedly arranged in the gas detector (1); and wherein the reflecting wall (3) is arranged at such a distance d from the wave generating and sensing means (2) that a magnitude of an output signal of the acoustic waves generated by the wave generating and sensing means (2) is less than a magnitude of the output signal of the acoustic waves generated by the wave generating and sensing means (2) when resonance occurs between the reflecting wall (3) and the wave generating and sensing means (2).

9. The gas detector (1) as claimed in claim 8, wherein the wave generating and sensing means (2) is arranged to generate acoustic waves having a constant frequency.

10. The gas detector (1) as claimed in claim 8, wherein the wave generating and sensing means (2) is arranged to generate acoustic waves with a frequency in the range 0.5 MHz to 500 MHz.

11. The gas detector (1) as claimed in claim 8, wherein the distance d is based on the resonance for acoustic waves propagating in a reference gas ($G_r$).

12. The gas detector (1) as claimed in claim 11, wherein the gas detector (1) comprises thermally expanding materials dimensioned such that thermo compensation is obtained in the gas detector (1).

13. The gas detector (1) as claimed in claim 8, wherein the wave generating and sensing means (2) comprises a piezoelectric resonator.

14. The gas detector (1) as claimed in claim 13, wherein the piezoelectric resonator comprises quartz or any other piezoelectric material.

15. The gas detector (1) as claimed in claim 8, wherein the distance d is in the range of approximately $\lambda/2$ to approximately $50*\lambda$, where $\lambda$ denotes the wavelength of the acoustic waves ($W_t$, $W_r$).

* * * * *

UNITED STATES PATENT AND TRADEMARK OFFICE
CERTIFICATE OF CORRECTION

PATENT NO.      : 9,267,924 B2
APPLICATION NO. : 13/640755
DATED           : February 23, 2016
INVENTOR(S)     : Mecca Page 1 of 1

It is certified that error appears in the above-identified patent and that said Letters Patent is hereby corrected as shown below:

In the Specification:

Column 5, Line 65: Please correct " $v = v_0 \sqrt{(1 + a\Delta t)}$ "

to read -- $v = v_0 \sqrt{(1 + \alpha \Delta t)}$ --

Signed and Sealed this
Twenty-sixth Day of July, 2016

Michelle K. Lee
*Director of the United States Patent and Trademark Office*